(12) United States Patent
Kozulin et al.

(10) Patent No.: US 9,518,279 B2
(45) Date of Patent: Dec. 13, 2016

(54) **BACTERIAL STRAIN *RHODOCOCCUS AETHERIVORANS* VKM AC-2610D PRODUCING NITRILE HYDRATASE, METHOD OF ITS CULTIVATION AND METHOD FOR PRODUCING ACRYLAMIDE**

(71) Applicant: Kemira Oyj, Helsinki OT (FI)

(72) Inventors: Sergey Vladimirovich Kozulin, Saratov (RU); Tatiana Nicolaevna Kozulina, Saratov (RU); Alexey Sergeevich Kozulin, Saratov (RU)

(73) Assignee: Kemira Oyj, Helsinki (FI)

(*) Notice: Subject to any disclaimer, the term of this patent is extended or adjusted under 35 U.S.C. 154(b) by 74 days.

(21) Appl. No.: 14/140,150

(22) Filed: Dec. 24, 2013

(65) Prior Publication Data

US 2014/0187818 A1 Jul. 3, 2014

(30) Foreign Application Priority Data

Dec. 27, 2012 (RU) .................. 2012157783

(51) Int. Cl.
*C12P 13/02* (2006.01)
*C12R 1/00* (2006.01)
*C12N 1/20* (2006.01)

(52) U.S. Cl.
CPC .......... *C12P 13/02* (2013.01); *C12N 1/20* (2013.01); *C12R 1/00* (2013.01); *C12Y 402/01084* (2013.01)

(58) Field of Classification Search
CPC .............. C12P 13/02; C12N 1/20; C12R 1/00
See application file for complete search history.

(56) References Cited

U.S. PATENT DOCUMENTS

| | | | |
|---|---|---|---|
| 5,089,411 A | 2/1992 | Yamada et al. | |
| 5,179,014 A | 1/1993 | Watanabe et al. | |
| 5,827,699 A | 10/1998 | Yanenko et al. | |
| 7,491,521 B2 | 2/2009 | Osswald et al. | |
| 7,575,912 B2 | 8/2009 | Hughes et al. | |
| 2005/0239165 A1 | 10/2005 | Lorenz et al. | |

FOREIGN PATENT DOCUMENTS

| | | |
|---|---|---|
| CN | 101186911 | 5/2008 |
| CN | 101892228 | 11/2010 |
| EP | 0362829 | 4/1990 |
| EP | 1689861 | 11/2011 |
| JP | 63137688 | 6/1988 |
| JP | 1074996 | 3/1989 |
| JP | 1171478 | 7/1989 |
| JP | 2001069978 | 3/2001 |
| RU | 1838408 | 8/1993 |
| RU | 2053300 | 1/1996 |
| RU | 2077588 | 4/1997 |
| RU | 2146291 | 3/2000 |
| RU | 2159817 | 11/2000 |
| RU | 2196822 | 1/2003 |
| RU | 2223316 | 2/2004 |
| RU | 2304165 | 8/2007 |
| RU | 2385932 | 4/2008 |
| RU | 2403280 | 11/2010 |
| RU | 2468084 | 11/2012 |
| SU | 1731814 | 5/1992 |
| WO | 2005054456 | 6/2005 |
| WO | 2006007957 | 1/2006 |

OTHER PUBLICATIONS

Extended European Search Report, EP Application No. 13199300.8, Mar. 18, 2014, 7 pages.
PCT International Search Report and Written Opinion of the International Searching Authority, PCT/IB2013/061268, Mar. 18, 2014, 8 pages.
PCT International Preliminary Report on Patentability, PCT/IB2013/061268, Jul. 9, 2015, 6 pages.
Kim et al., "Fed-Batch Fermentation for Production of Nitrile Hydratase by Rhodococcus Rhodochrous M33", Biotechnol. Bioprocess Eng., Published in 2001, vol. 6, No. 1, 8 pages.
Goodfellow et al., "*Rhodococcus aetherivorans* SP. Nov., A New Species that Contains Methyl t-butyl Ether-Degrading Actinomycetes", Systematic and Applied Microbiology, published in 2004, vol. 27, 5 pages.

*Primary Examiner* — Scott Long
*Assistant Examiner* — Sean C Barron
(74) *Attorney, Agent, or Firm* — Fish & Richardson P.C.

(57) ABSTRACT

The invention relates to a bacterial strain belonging to the genus *Rhodococcus* which is a producer of a nitrile hydratase. The invention also relates to a method for producing acrylamide by hydration of acrylonitrile using a biomass of the bacterial strain and to a method of culturing the bacterial strain.

20 Claims, No Drawings

**BACTERIAL STRAIN *RHODOCOCCUS AETHERIVORANS* VKM AC-2610D PRODUCING NITRILE HYDRATASE, METHOD OF ITS CULTIVATION AND METHOD FOR PRODUCING ACRYLAMIDE**

FIELD OF THE INVENTION

The group of inventions relates to a biotechnology and microbiological industry and includes:
  a new strain of bacterium *Rhodococcus aetherivorans* having a high nitrile hydratase enzyme activity;
  a method of its cultivation;
  a method for producing concentrated solutions of acrylamide using cells of the strain as a biocatalyst.

BACKGROUND OF THE INVENTION

The ability of microorganisms to transform carbonitriles to corresponding amides was described in literature at the beginning of $70^{th}$ years of the XX century. Nitrile hydratase enzyme catalyzing such reactions is inherent to a wide range of bacteria relating to various taxonomical groups. Representatives of the genus *Rhodococcus* are of practical interest with respect to the subject of the present specification. Large chemical and biotechnological companies of Japan, Korea, France, Russia, Germany, the USA and China use, inter alia, cells of strains belonging to this genus as effective biocatalysts for acrylamide production.

Despite deep investigations of the process of the enzymatic hydrolysis of nitriles to corresponding amides and considerable successes in the field of selection of strains producing nitrile hydratase, the industry demand for new biocatalysts has not dropped. This is caused, on the one hand, by the efficacy and ecological safety of biotechnological production of amides, in particular acrylamide, and on the other hand by a high cost of earlier patented strains and technologies. Therefore in recent years new microorganisms which were producers of a nitrile hydratase enzyme were isolated.

Known bacterial strains and methods for producing acrylamide using such strains, however, suffer from several drawbacks. Many strains are only capable of producing a maximum concentration of less than 40% of acrylamide, and therefore the use of such strains is limited.

Another disadvantage of certain strains is the components that are expensive and vary in composition, such as vitamins, peptone or yeast extract, must be included in their cultivation medium. Some strains exhibit only low nitrile hydratase activity. To increase activity, additional steps such as removal of oxygen from the culture broth together with the enzyme activation during several days may be required.

Some strains require a cultivation medium that contains toxic components. For instance, acetonitrile may be required in the cultivation medium, but acetonitrile is toxic, volatile, highly inflammable and expensive.

SUMMARY

The disclosure relates, in part, to the bacterial strain *Rhodococcus aetherivorans* VKM Ac-2610D.

The disclosure relates, in part, to a method for producing acrylamide.

The disclosure relates, in part, to a method of culturing the bacterial strain described herein.

The disclosure relates, in part, to a final product obtained by the methods described herein.

DETAILED DESCRIPTION

The present invention relates to a bacterial strain *Rhodococcus aetherivorans* VKM Ac-2610D.

In an embodiment, the bacterial strain *Rhodococcus aetherivorans* VKM Ac-2610D is a producer of a nitrile hydratase.

The present patent application relates also to a method of cultivating the bacterial strain *Rhodococcus aetherivorans* VKM Ac-2610D.

The present application relates also to a method of producing acrylamide.

An object of the claimed group of inventions is the creation of a new bacterial strain having a high nitrile hydratase activity for use in the industrial production of merchantable products.

An object of the claimed method of cultivating the strain is the development of a technology for the biomass production of the claimed strain without a superfluous cost, moreover, if possible, with a cost reduction compared with the existing similar methods that are used in industry.

An object of the claimed method of producing the referred product by use of a new strain is the development of a technology for producing acrylamide at a predetermined concentration by use of the new strain without increasing the process cost and without additional complication of process operations.

The present invention also relates to a method of culturing a bacterial strain *Rhodococcus aetherivorans* VKM Ac-2610D, wherein cells of the strain are cultured using a nutrient medium comprising
  an aqueous phosphate buffer comprising sodium and potassium ions;
  a source of carbon;
  a source of nitrogen;
  optionally an enzyme inducer;
  optionally a cobalt salt;
  a magnesium salt;
  a zinc salt;
  a calcium salt; and
  a Fe(II) salt.

In an embodiment, the nutrient medium comprises
  an aqueous phosphate buffer comprising sodium and potassium ions;
  a source of carbon;
  a source of nitrogen;
  an enzyme inducer;
  a cobalt salt;
  a magnesium salt;
  a zinc salt;
  a calcium salt; and
  a Fe(II) salt.

In an embodiment, the nutrient medium consists of
  an aqueous phosphate buffer comprising sodium and potassium ions;
  a source of carbon;
  a source of nitrogen;
  optionally an enzyme inducer;
  optionally a cobalt salt;
  a magnesium salt;
  a zinc salt;
  a calcium salt; and
  a Fe(II) salt.

In an embodiment, the nutrient medium consists of
an aqueous phosphate buffer comprising sodium and potassium ions;
a source of carbon;
a source of nitrogen;
an enzyme inducer;
a cobalt salt;
a magnesium salt;
a zinc salt;
a calcium salt; and
a Fe(II) salt.

In an embodiment, the cells of the strain are cultured in the nutrient medium.

In an embodiment, the cells of the strain are suspended in the nutrient medium during the culturing.

In an embodiment, the pH of the nutrient medium is 6.3-8.3. In an embodiment, the pH of the nutrient medium is 7.0-7.4.

In an embodiment, the process is carried out at a temperature of 26-31° C. In an embodiment, the process is carried out at a temperature of 28-30° C. In this context, the term "the process" should be understood as referring to the process of culturing the cells of the strain using the nutrient medium.

In an embodiment, the cells of the bacterial strain are cultured with stirring.

In an embodiment, the cells of the bacterial strain are cultured with aeration.

In an embodiment, the cells of the bacterial strain are cultured until the growth of the cells of the bacterial strain enters the stationary phase.

In an embodiment, the cells of the bacterial strain are cultured until a predetermined yield of cells of the bacterial strain is achieved.

The predetermined yield may vary e.g. depending on the amount of biomass that should be obtained for the process of producing acrylamide, or on the nitrile hydratase activity of the cells of the bacterial strain.

The achievement of a predetermined yield of cells may be determined by known methods such as measurement of optical density of the culture or measurement of the dry weight of the cell mass. Optical density, or absorbance, may be measured e.g. in a photoelectric colorimeter as described below. Likewise, said methods may be used to determine when the growth of the cells of the bacterial strain enters the stationary phase.

In an embodiment, the cells of the bacterial strain are cultured until the achievement of an optical density of the suspension of 36-40. In this context, the "suspension" should be understood as referring to the nutrient medium comprising the cells of the bacterial strain suspended therein.

The optical density of the suspension of 36-40 indicates that bacterial growth has reached the stationary phase. Herein and in the Examples, the optical density is measured in a photoelectric colorimeter with a thickness of optical layer of 5 mm at the wavelength 540 nm. Photoelectric colorimeters or spectrophotometers suitable for measuring optical density are well known in the art.

In an embodiment, the process is carried out until the achievement of an optical density of the suspension of 36-40.

In an embodiment, the process is carried out until the achievement of an optical density of the suspension of 36-40 at a wavelength of 540 nm and a thickness of an optical layer 5 mm.

The aqueous phosphate buffer may be any aqueous phosphate buffer known in the art, provided it comprises sodium ($Na^+$) and potassium ($K^+$) ions. Said aqueous phosphate buffer may be prepared using various phosphate salts of sodium and potassium. In an embodiment, the aqueous phosphate buffer comprises a phosphate salt. In an embodiment, the aqueous phosphate buffer comprises a phosphate salt selected from the group consisting of $Na_2HPO_4$, $NaH_2PO_4$, $KH_2PO_4$, $K_2HPO_4$ and any mixtures thereof. In an embodiment, the aqueous phosphate buffer comprises $Na_2HPO_4.12H_2O$ and $KH_2PO_4$. The pH of the aqueous phosphate buffer may be selected so as to adjust the pH of the nutrient medium to 6.3-8.3 or to 7.0-7.4.

In an embodiment, the source of carbon is selected from the group consisting of glucose, cellobiose, fructose, galactose, maltose, mannose, sucrose, trehalose, ribose, glycerol, mannitol, sorbitol, salicin, inulin, citrate, pyruvate, succinate, fumarate and any mixtures thereof.

In an embodiment, the source of carbon is glucose.

In an embodiment, the nutrient medium comprises 20.0-60.0 g/l of the source of carbon.

The source of nitrogen may be any source of nitrogen the cells of the bacterial strain are able to utilize. Many suitable sources of nitrogen are also capable of inducing nitrile hydratase activity. A skilled person will therefore understand that a single compound may be included in the nutrient medium both as a source of nitrogen and as an enzyme inducer. In an embodiment, the source of nitrogen is selected from the group consisting of carbamide, leucine, acetamide or any mixture thereof. In an embodiment, the source of nitrogen is carbamide.

In this context, the words "enzyme inducer" and "inducer" may be used interchangeably and refer to an agent capable of inducing nitrile hydratase activity. Several enzyme inducers capable of inducing nitrile hydratase activity are known in the art. In an embodiment, the enzyme inducer is carbamide. In an embodiment, the enzyme inducer is an aliphatic amide. In an embodiment, the enzyme inducer is selected from the group consisting of propionamide, isobutyramide, acetamide and a mixture thereof.

In an embodiment, the source of nitrogen and the inducer is carbamide. Carbamide (urea) may be utilized as a microorganism-friendly source of nitrogen and is readily available for industrial purposes. It can also function as an enzyme inducer.

In an embodiment, the nutrient medium comprises 10.0-24.0 g/l of the source of nitrogen.

The cobalt salt may be any soluble cobalt salt. Cobalt ions are utilized as cofactors for the nitrile hydratase enzyme. In an embodiment, the cobalt salt is $CoCl_2$, $CoSO_4$ or a mixture thereof. In an embodiment, the cobalt salt is $CoCl_2.6H_2O$, $CoSO_4.7H_2O$ or a mixture thereof. In an embodiment, the nutrient medium comprises 0.04-0.085 g/l of the cobalt salt.

The magnesium salt may be any soluble magnesium salt. Magnesium ions provided by the magnesium salt are utilized in transport functions of the cells of the bacterial strain. In an embodiment, the magnesium salt is $MgSO_4$. In an embodiment, the magnesium salt is $MgSO_4.7H_2O$. In an embodiment, the nutrient medium comprises 10.0-24.0 g/l of the magnesium salt.

The zinc salt may be any soluble zinc salt. Zinc ions provided by the zinc salt may be utilized in decomposition of the nitrogen source such as carbamide. In an embodiment, the zinc salt is $ZnSO_4$. In an embodiment, the zinc salt is $ZnSO_4.7H_2O$. In an embodiment, the nutrient medium comprises 0.08-0.4 g/l of the zinc salt.

The calcium salt may be any soluble calcium salt. Calcium ions provided by the calcium salt may be involved in the utilization of the carbon source such as glucose. In an embodiment, the calcium salt is selected from the group consisting of $CaCl_2$, $CaHPO_4.2H_2O$, $Ca(H_2PO_4)_2.2H_2O$, $Ca_3(PO_4)_2$, $CaCl_2.2H_2O$, $CaCO_3$, $CaSO_4$, $Ca(C_3H_5O_3)_2.3H_2O$, $Ca(HOCH_2(CHOH)_4COO)_2.H_2O$ and any mixtures thereof. In an embodiment, the nutrient medium comprises 0.2-0.6 g/l of the calcium salt.

The Fe(II) salt may be any soluble Fe(II) salt. Ferrous ions provided by the salt are utilized in respiration. In an embodiment, the Fe(II) salt is in a chelate complex form. In an embodiment, the Fe(II) salt is $FeSO_4$ in a chelate complex form. In an embodiment, the Fe(II) salt is $FeSO_4.7H_2O$ in a chelate complex form. In an embodiment, the nutrient medium comprises 0.025-0.05 g/l of the Fe(II) salt.

In an embodiment, the magnesium salt is $MgSO_4$; the zinc salt is $ZnSO_4$; the calcium salt is selected from the group consisting of $CaCl_2$, $CaHPO_4.2H_2O$, $Ca(H_2PO_4)_2.2H_2O$, $Ca_3(PO_4)_2$, $CaCl_2.2H_2O$, $CaCO_3$, $CaSO_4$, $Ca(C_3H_5O_3)_2.3H_2O$, $Ca(HOCH_2(CHOH)_4COO)_2.H_2O$ any any mixtures thereof; and the Fe(II) salt is $FeSO_4.7H_2O$ in a chelate complex form.

The source of carbon, the source of nitrogen, the inducer, and the cobalt salt may be introduced in the nutrient medium in one portion or in several portions during the culturing and cell growth.

The nutrient medium is simple and cheap to manufacture. It also allows for a high yield of biomass of the bacterial strain and high activity of nitrile hydratase in the biomass of the bacterial strain.

In an embodiment, the nutrient medium does not comprise vitamins, amino acids, peptones, plant extracts, yeast extracts and/or acetonitrile.

The produced biomass may subsequently be separated. Methods for separating the produced biomass are well known in the art.

In an embodiment, the cells of the strain are seeded on a solid nutrient medium and cultivated for a time period, then the biomass is washed out, and the resulting suspension is used for inoculation of a first vessel comprising the nutrient medium, and the process is carried out during a time period with stirring to achieve an optical density of the suspension in the range of 2-16 units at a wavelength of 540 nm and a thickness of an optical layer 5 mm; then the resulting suspension is used for inoculation of a second vessel having a volume which is 10-100 times larger than a volume of the first vessel, the second vessel comprising new nutrient medium, to achieve optical density of 0.1-0.3 in the second vessel; the process is continued for a time period with aeration until the achievement of an optical density of the suspension of 36-40 and a pH of 7.5-7.8; then the produced biomass is separated.

In an embodiment, the cells of the strain are seeded on a solid nutrient medium and cultivated for 24-48 hours, then the biomass is washed out, and a resulting suspension is used for inoculation of a first vessel comprising the nutrient medium, and the process is carried out during 24-48 hours with stirring to achieve an optical density of the suspension in the range of 2-16 units at a wavelength of 540 nm and a thickness of an optical layer 5 mm, then the resulting suspension is used for inoculation of a second vessel having a volume which is 10-100 times larger than a volume of the first vessel, the second vessel comprising new nutrient medium, to achieve optical density of 0.1-0.3 in the second vessel; the process is continued for 48-120 hours with aeration until the achievement of an optical density of the suspension of 36-40 and a pH of 7.5-7.8; then the produced biomass is separated.

The cells of the bacterial strain may be cultured as a one-step cultivation, wherein the cells of the bacterial strain are cultured in the nutrient medium until a first predetermined yield of cells is achieved. The cells of the bacterial strain may also be cultured as a two-step cultivation, wherein the cells of the bacterial strain are cultivated in the nutrient medium in a first vessel and subsequently using the resulting culture or suspension to inoculate a new nutrient medium in a second vessel; the cells of the bacterial strain are cultured in the new nutrient medium until a second predetermined yield of cells is achieved. The first and second predetermined yield need not be the same. Typically, the first predetermined yield need not be as high as the second predetermined yield.

The two-step cultivation, wherein the cells of the strain are cultured in the first vessel in a first step and in the second vessel as a second step may allow for better adaptation of the bacterial strain to the medium and improved enzyme synthesis.

The solid nutrient medium may be e.g. a meat and peptone agar, LB medium agar, a synthetic medium or any other solid nutrient medium which is capable of supporting the growth of the bacterial strain Rhodococcus aetherivorans VKM Ac-2610D.

The biomass may be washed out e.g. with a sterile physiological solution such as phosphate-buffered saline. The sterile physiological solution may have a pH of 7.0-7.4.

The stirring of the first vessel may be e.g. circular stirring at a rate of 140-160 rpm.

In this context, the term "new nutrient medium" should be understood as referring to a fresh volume of the nutrient medium defined above.

The invention also relates to a method of cultivating the bacterial strain Rhodococcus aetherivorans VKM Ac-2610D wherein cells of the strain are seeded on a meat and peptone agar slope and cultivated for 24-48 hours, then a biomass is washed out with a sterile physiological solution having a pH of 7.0-7.4, and a resulting suspension is used for inoculating a first vessel comprising a nutrient medium of the following composition, g/l:

| | |
|---|---|
| $Na_2HPO_4 \cdot 12H_2O$ | 6.06 |
| $KH_2PO_4$ | 1.3 |
| glucose | 10.0-20.0 |
| carbamide | 2.0-6.0 |
| $MgSO_4 \cdot 7H_2O$ | 1.0 |
| $ZnSO_4 \cdot 7H_2O$ | 0.08-0.2 |
| $CaCl_2 \cdot 2H_2O$ | 0.2 |
| $CoCl_2 \cdot 6H_2O$ | 0.01-0.02 |
| $FeSO_4 \cdot 7H_2O$ in a chelate complex form | 0.01-0.025 |
| Distilled water | to 1 l | pH 7.0-7.4;

and the process is carried out during 24-48 hours at a temperature of 28-30° C. with a circular stirring at a rate of 140-160 rpm to achieve optical density of the suspension in the range of 2-16 units at a wavelength 540 nm with a thickness of optical layer 5 mm. Then the resulting suspension is used for inoculating a second vessel having a volume which is 10-100 times larger than a volume of the first vessel, the second vessel comprising a new nutrient medium of the following composition, g/l:

| | |
|---|---|
| Na$_2$HPO$_4$•12H$_2$O | 6.20 |
| KH$_2$PO$_4$ | 1.65 |
| glucose | 20.0-60.0 |
| carbamide | 10.0-24.0 |
| MgSO$_4$•7H$_2$O | 0.8-1.0 |
| ZnSO$_4$•7H$_2$O | 0.08-0.4 |
| a calcium salt | 0.2-0.6 |
| a cobalt salt | 0.04-0.085 |
| FeSO$_4$•7H$_2$O in a chelate complex form | 0.025-0.05 |
| distilled water | to 1 l | pH 7.0-7.4;

to achieve optical density of 0.1-0.3 in the second vessel; the process is continued for 48-120 hours at a temperature of 26-31° C., an aeration of 0.5-1.0 volume of air/volume of medium per a minute until achievement of a suspension optical density of 36-40 and a pH of 7.5-7.8; then the obtained biomass is separated.

In an embodiment of the above described method of cultivating the bacteria strain *Rhodococcus aetherivorans* VKM Ac-2610D, the nutrient medium in the second vessel may comprise one of the following salts as a calcium salt:

CaHPO$_4$.2H$_2$O
Ca(H$_2$PO$_4$)$_2$.2H$_2$O
Ca$_3$(PO$_4$)$_2$
CaCl$_2$.2H$_2$O
CaCO$_3$
CaSO$_4$
Ca(C$_3$H$_5$O$_3$)$_2$.3H$_2$O
Ca(HOCH$_2$(CHOH)$_4$COO)$_2$.H$_2$O;

and one of following salts as a cobalt salt: CoCl$_2$.6H$_2$O, CoSO$_4$.7H$_2$O.

The present invention also relates to a method for producing acrylamide by hydration of ac-rylonitrile using a biomass of a strain belonging to the genus *Rhodococcus* and having a nitrile hydratase activity, wherein the hydration is carried out at a working concentration of acrylonitrile which is no more than 0.5%, using a biomass of the bacterial strain *Rhodococcus aetherivorans* VKM Ac-2610D.

A final product containing acrylamide is obtained by the method.

In an embodiment, the hydration is followed by isolation of the final acrylamide product.

The term "final acrylamide product" should be understood as referring to acrylamide contained in the final product. Methods that are suitable for isolating acrylamide from the final product are known in the art.

Acrylonitrile is a toxic compound, and a suitable working concentration thereof that is not overly toxic to the bacterial strain should be main-tained. A working concentration of acrylonitrile which is no more than 0.5% is tolerated by the bacterial strain. Said working concentration may also allow for obtaining acrylamide in the final product at a concentration of 45-49%. The working concentration may be maintained by loading acrylonitrile in the reaction solution during the hydration reaction. A skilled person may select the working concentration of acrylonitrile e.g. so that the hydration rate or the amount of the final acrylamide product is optimal. In an embodiment, the working concentration of acrylonitrile is in the range of 0.01-0.5%, or 0.05-0.5%, or 0.1-0.5%.

In an embodiment, the working concentration of acrylonitrile is no more than 0.5%, or in the range of 0.01-0.5%, or 0.05-0.5%, or 0.1-0.5% by weight based on the total weight of the reaction solution (w/w).

In this context, the term "working concentration" should be understood as referring to the concentration in the reaction solution comprising the biomass of the bacterial strain and acrylonitrile. The reaction solution may also comprise other components, such as water, acrylamide and/or any additives.

The term "reaction solution" should be understood as referring to the reaction mixture comprising the biomass of the bacterial strain and acrylonitrile. The reaction mixture may also comprise other components, such as water, acrylamide and/or any additives.

The amount of the biomass of the bacterial strain used may be selected e.g. so that the hydration rate or the amount of the final acrylamide product is optimal. The amount of the biomass of the bacterial strain may depend e.g. on the nitrile hydratase activity of the cells of the bacterial strain.

In an embodiment, the biomass of the bacterial strain *Rhodococcus aetherivorans* VKM Ac-2610D is at about 100-1000 g, or 200-1000 g, or 200-800 g, or 300-600 g, or less than 1000 g, or less than 500 g, or less than 400 g on a dry weight of strain per 1 ton of the final product.

In an embodiment, the biomass of the bacterial strain *Rhodococcus aetherivorans* VKM Ac-2610D is at about 400-500 g on a dry weight of strain per 1 ton of the final product.

In this context, the term "the final product" should be understood as referring to the reaction solution comprising the biomass of the strain and acrylamide. The final product may also comprise other components, e.g. water, minor amounts of acrylonitrile and/or any additives. A skilled person will understand that the acrylonitrile included in the reaction solution is hydrated into acrylamide by the biomass of the bacterial strain. In other words, the final product refers to the entire reaction solution in which the acrylonitrile added in the reaction solution has been hydrated into acrylamide.

The term "biomass" should be understood as referring to a mass of cells of the bacterial strain.

In an embodiment, the final product contains acrylamide at a concentration of at least 40%; or at least 41%; or at least 42%; or at least 43%; or at least 44%; or 40-55%; or 41-55%; 42-55%; or 43-55%; or 44-55%.

In an embodiment, the final product contains acrylamide at a concentration of at least 45%; or at least 46%; or at least 47%; or 45-55%; or 45-54%; or 45-53%; or 45-52%; or 45-51%; or 45-50%; or 45-49%; or 46-55%; or 46-54%; or 46-53%; or 46-52%; or 46-51%; or 46-50%; or 46-49%; or 47-55%; or 47-54%; or 47-53%; or 47-52%; or 47-51%; or 47-50%; or 47-49%.

In an embodiment, the final product contains acrylamide at a concentration of at least 40%; or at least 41%; or at least 42%; or at least 43%; or at least 44%; or 40-55%; or 41-55%; 42-55%; or 43-55%; or 44-55%; or at least 45%; or at least 46%; or at least 47%; or 45-55%; or 45-54%; or 45-53%; or 45-52%; or 45-51%; or 45-50%; or 45-49%; or 46-55%; or 46-54%; or 46-53%; or 46-52%; or 46-51%; or 46-50%; or 46-49%; or 47-55%; or 47-54%; or 47-53%; or 47-52%; or 47-51%; or 47-50%; or 47-49% by weight on the basis of the total weight of the final product.

In an example corresponding to Example 6, in order to obtain acrylamide at a concentration of 47% in the final product, 757.2 g of acrylonitrile may be introduced into a reactor, resulting in a total reaction mass of 2157.2 g. Since all acrylonitrile is transformed by the cells of the bacterial strain to acrylamide, a final concentration of 47% of acrylamide is obtained in the final product. The reaction would, in this example, include 1 g of biomass (dry weight).

In an embodiment, the hydration of acrylonitrile is carried out at a temperature of 10-23° C.

In an embodiment, the hydration of acrylonitrile is carried out at a pH of 6.8-8.4.

In an embodiment, the hydration of acrylonitrile is carried out at a temperature of 10-23° C. and at a pH of 6.8-8.4.

In an embodiment, a biomass of the bacterial strain is suspended in aqueous solution; and acrylonitrile is added in the aqueous solution to form a reaction solution.

In an embodiment, acrylonitrile is mixed in an aqueous suspension of a biomass of the bacterial strain *Rhodococcus aetherivorans* VKM Ac-2610D to form a reaction solution; and hydration is carried out so that the working concentration of acrylonitrile in the reaction solution is maintained at no more than 0.5%.

In an embodiment, the method comprises the following steps:

a) a biomass of the bacterial strain *Rhodococcus aetherivorans* VKM Ac-2610D is suspended in aqueous solution to obtain a suspension;

b) acrylonitrile is mixed in the suspension obtainable from step a) to form a reaction solution; and c) hydration is carried out so that the working concentration of acrylonitrile in the reaction solution is maintained at no more than 0.5%.

In an embodiment, the working concentration of acrylonitrile in the reaction solution is main-tained at no more than 0.5% until a final product containing acrylamide at a concentration of at least 45% is obtained.

In an embodiment of the method including the hydration of acrylonitrile using a biomass of a strain belonging to the genus *Rhodococcus*, having nitrile hydratase activity, and then isolation of the final product, i.e. acrylamide, the hydration is carried out at a working concentration of acrylonitrile no more than 0.5%, using a biomass of the bacterial strain *Rhodococcus aetherivorans* VKM Ac-2610D in an amount of about 400-500 g on the dry weight basis of the strain per 1 ton of the final product that is acrylamide at a concentration of 45-49%.

The present invention also relates to the final product obtainable by one or more embodiments of the method for producing acrylamide.

In an embodiment, the final product comprises a biomass of the bacterial strain and acrylamide. The final product may further comprise other components, e.g. water, minor amounts of acrylonitrile and/or any additives.

In an embodiment, the final product contains acrylamide at a concentration of at least 40%; or at least 41%; or at least 42%; or at least 43%; or at least 44%; or 40-55%; or 41-55%; 42-55%; or 43-55%; or 44-55%.

In an embodiment, the final product contains acrylamide at a concentration of at least 45%; or at least 46%; or at least 47%; or 45-55%; or 45-54%; or 45-53%; or 45-52%; or 45-51%; or 45-50%; or 45-49%; or 46-55%; or 46-54%; or 46-53%; or 46-52%; or 46-51%; or 46-50%; or 46-49%; or 47-55%; or 47-54%; or 47-53%; or 47-52%; or 47-51%; or 47-50%; or 47-49%.

In an embodiment, the final product contains acrylamide at a concentration of at least 40%; or at least 41%; or at least 42%; or at least 43%; or at least 44%; or 40-55%; or 41-55%; 42-55%; or 43-55%; or 44-55%; or at least 45%; or at least 46%; or at least 47%; or 45-55%; or 45-54%; or 45-53%; or 45-52%; or 45-51%; or 45-50%; or 45-49%; or 46-55%; or 46-54%; or 46-53%; or 46-52%; or 46-51%; or 46-50%; or 46-49%; or 47-55%; or 47-54%; or 47-53%; or 47-52%; or 47-51%; or 47-50%; or 47-49% by weight on the basis of the total weight of the final product.

The present invention also relates to acrylamide obtainable from the final product.

The technical result provided by the claimed group of inventions.

The strain of bacteria *Rhodococcus aetherivorans* VKM Ac-2610D is characterized in that it grows on a simple organo-mineral medium and has a high nitrile hydratase activity up to 332 U/mg at 20° C. or 521 U/mg at 25° C. Nitrile hydratase of the bacterial strain *Rhodococcus aetherivorans* VKM Ac-2610D is thermostable.

The strain was isolated from wastewaters of the acrylamide and polyacrylamide manufacture and was not genetically modified. It is especially important for its use as an industrial biocatalyst because a legislation of many countries limits the use of genetically modified microorganisms.

The developed method of cultivating a bacterial strain *Rhodococcus aetherivorans* VKM Ac-2610D makes it possible to have a high yield of cells having high activity on a simple organo-mineral nutrient medium, which does not comprise expensive inducers, vitamins, amino acids and plant extracts. Since all the components of the nutrient medium are commercially available, the cost of the industrial biocatalyst prepared on the basis of the claimed strain is reduced. The method for cultivation according to one or more embodiments is optimal for rapid growth of the bacterial strain. Furthermore, the method for cultivation according to one or more embodiments may be used to provide a biomass of the bacterial strain that can be used in the method for producing acrylamide according to one or more embodiments.

The method for producing acrylamide by its synthesis using the bacterial strain *Rhodococcus aetherivorans* VKM Ac-2610D described in this application is economically advantageous. Conditions of synthesis of concentrated solutions of acrylamide are optimized.

The claimed strain is isolated from wastewaters of the acrylamide and polyacrylamide manufacture by a method of direct seeding on a selective medium.

The claimed strain of bacteria *Rhodococcus aetherivorans* is deposited under the Budapest Treaty by Individual entrepreneur Sergey Kozulin in the AllRussian Collection of Microorganisms (Russian Collection of Microorganisms (VKM), G.K. Skryabin Institute of Biochemistry and Physiology of Microorganisms, Russian Academy of Sciences, Prospekt Nauki No. 5, Pushchino 142290 (Moscow Region), Russian Federation) with an accession number VKM Ac-2610D (identification reference given by the depositor: *Rhodococcus aetherivorans* KTN26-1). The strain was received by the Depositary Authority on 20, Jul. 2012, and the deposit was converted into a deposit under the Budapest Treaty on 15, Nov. 2013. The strain is characterized by the following morphological, culture and biochemical properties.

Morphological properties: a gram-positive strain having a life cycle of *Rhodococcus*, non-motile, non-sporeforming, is not encysting, is acidintolerant, aerobic.

Culture properties: it forms round smooth colonies on meat and peptone agar, having from yellow-orange to red-orange color and a diameter of 1-2 mm (after 72-96 hours). When grown on special media it dissociates to R- , S- and M-forms.

Physiological properties: The strain is oxidase-negative, catalase- and phosphatase-positive, reduces nitrates into nitrites. It hydrolyzes starch, Tween 60 and Tween 80; it does not hydrolyze cellulose, esculin and DNA. It grows at a pH of 5.5-9.5, optimal pH value being 7.2±0.2; at a temperature of 5-45° C., optimal value being 29±1° C. As a sole source of carbon it uses: a cellobiose, fructose, galactose, glucose, maltose, mannose, sucrose, trehalose, ribose, glycerol, mannitol, sorbitol, but it does not use dulcitol and inositol. The strain grows on a salicin, inulin, citrate, pyruvate, succinate, fumarate, but does not grow on a gluconate. It utilizes meta- and para-hydroxybenzoic acids, isobutanol, 2,3-butyleneglycol, monoethanol amine. It uses leucine and acetamide as a sole source of nitrogen.

Pathogenicity: the strain is not pathogenic.

On the basis of the above properties, according to Bergey's Manual of Determinative Bacteriology (Opredelitel bakteriy Berdgy, Moscow: Mir, 1997) and restriction fragment length polymorphism analysis of a gene 16S of a ribosomal ribonucleic acid, the strain is attributed to the genus Rhodococcus, aetherivorans species.

The method of cultivating the bacterial strain *Rhodococcus aetherivorans* VKM Ac-2610D may be carried out as follows.

Cells of the strain *Rhodococcus aetherivorans* stored at temperature of 4° C. in stabs of 0.4% agarized LB medium or meat and peptone broth may be seeded on a meat peptone agar slope and cultivated for 24-48 hours. The obtained biomass may be washed out with a sterile physiological solution having a pH of 7.0-7.4. The obtained suspension can be used for inoculation of a first vessel comprising a nutrient medium of the following composition, g/l:

| | |
|---|---|
| $Na_2HPO_4 \cdot 12H_2O$ | 6.06 |
| $KH_2PO_4$ | 1.3 |
| glucose | 10.0-20.0 |
| carbamide | 2.0-6.0 |
| $MgSO_4 \cdot 7H_2O$ | 1.0 |
| $ZnSO_4 \cdot 7H_2O$ | 0.08-0.2 |
| $CaCl_2 \cdot 2H_2O$ | 0.2 |
| $CoCl_2 \cdot 6H_2O$ | 0.01-0.02 |
| $FeSO_4 \cdot 7H_2O$ in a chelate complex form | 0.01-0.025 |
| Distilled water | to 1 l | pH 7.0-7.4;

The process can be carried out during 24-48 hours at a temperature 28-30° C. with a circular stirring at a rate of 140-160 rpm to achieve optical density of the suspension in the range of 2-16 units measured in a photoelectric colorimeter with a thickness of optical layer of 5 mm at the wavelength 540 nm.

Then the resulting suspension may be used for inoculating a second (larger) vessel having a volume which is 10-100 times larger than a volume of the first vessel, e.g. a large flask or fermenter comprising a new nutrient medium of the following composition, g/l:

| | |
|---|---|
| $Na_2HPO_4 \cdot 12H_2O$ | 6.20 |
| $KH_2PO_4$ | 1.65 |
| glucose | 20.0-60.0 |
| carbamide | 10.0-24.0 |
| $MgSO_4 \cdot 7H_2O$ | 0.8-1.0 |
| $ZnSO_4 \cdot 7H_2O$ | 0.08-0.4 |
| a calcium salt | 0.2-0.6 |
| a cobalt salt | 0.04-0.085 |
| $FeSO_4 \cdot 7H_2O$ in a chelate complex form | 0.025-0.05 |
| distilled water | to 1 l | pH 7.0-7.4.

The nutrient medium in the second vessel may comprise one of following salts as a calcium salt: $CaHPO_4 \cdot 2H_2O$, $Ca(H_2PO_4)_2 \cdot 2H_2O$, $Ca_3(PO_4)_2$, $CaCl_2 \cdot 2H_2O$, $CaCO_3$, $CaSO_4$, $Ca(C_3H_5O_3)_2 \cdot 3H_2O$, $Ca(HOCH_2(CHOH)_4COO)_2 \cdot H_2O$; and one of following salts as a cobalt salt: $CoCl_2 \cdot 6H_2O$, $CoSO_4 \cdot 7H_2O$.

Glucose, carbamide and cobalt salts can be introduced in the nutrient medium in one portion or in several portions during the cell growth.

The value of optical density in the second vessel may be brought to 0.1-0.3units. The process may be continued for 48-120 hours at a temperature of 26-31° C., an aeration of 0.5-1.0 volume of air/volume of medium per a minute until the achievement of an optical density of the suspension in the range of 36-40 and a pH of 7.5-7.8. After the end of the process, thebiomass is separated by any known method such as centrifugation, flocculation, flotation, sedimentation with the following filtration. Implementation of this method of cultivating strain *Rhodococcus aetherivorans* VKM Ac-2610D can give a cell yield of 10-18 g/l with the activity of nitrile hydratase enzyme of 250-332 U/mg. The biomass can be used later in processes of producing acrylamide.

Testing the activity of nitrile hydratase enzyme may be carried out as follows: a suspension of cells is prepared in 0.01 M phosphate buffer, pH 7.6, at a concentration of 0.04-0.06 mg of cells (on a dry weight basis)/ml. The acrylonitrile substrate in the amount of 25 µl is introduced into 1 ml of suspension. A transformation reaction is carried out in a water bath at a temperature of 20-25° C. and with a stirring for 10 min. The reaction is stopped by adding 50 µl of 6H HCl. Bacterial cells are separated by centrifugation. The concentration of acrylamide in a supernatant is determined by a spectrophotometric or gas chromatographic method. Activity measurements of nitrile hydratase described herein and in the Examples have been performed at a temperature of 20° C. unless otherwise indicated.

A unit of a specific nitrile hydratase activity (U/mg) is an amount of the enzyme catalyzing generation of 1 µM of acrylamide per unit of time (1 minute) in 1 mg of cells (on a dry weight basis). A unit of a total nitrile hydratase activity (U/ml) is an amount of enzyme units contained in 1 ml of a culture broth.

In detail, the method of producing acrylamide may be carried out as follows.

Cells of bacterial strain *Rhodococcus aetherivorans* VKM Ac-2610D obtained as indicated in the description of the method of cultivation, may be separated from the culture broth according to any known method, washed with desalted water, pH 7.0-7.6. The amount of water which can be used for washing may be 1-10 volumes/volume of cells. The washed cells can be suspended in a tap or distilled water, pH 6.8-8.4, at about 400-500 g of cells (on dry weight basis) per 1 ton of the final product, i.e. 45-49% solution of acrylamide may be prepared depending on the intended concentration of a final product and time of synthesis. The water suspension of cells can be placed in a thermostatic reactor. The reaction of acrylamide synthesis may be carried out in the range of pH 6.8-8.4. Acrylonitrile may be loaded into the reaction solution during transformation so that its concentration in the solution is no more than 0.5%. The reaction mixture may be constantly stirred. The temperature of the reaction solution can be maintained in the range of 10-23° C. Time of reaction may be 5-8 hours. Acrylamide and acrylonitrile in the reaction solution may be analyzed by any known method, for example liquid or gas chromatography, spectrophotometry, refractometry. The analysis can be carried out at least once an hour. The process can be stopped after a sudden drop of a rate of acrylonitrile hydrolysis. After termination of the process cells of the biocatalyst may be separated from the reaction mixture by any known method, for example by a flocculation, filtration, flotation, centrifugation. The process can give solutions having a concentration of acrylamide of e.g. 45-49%.

A skilled person will understand that the methods may be scaled so as to cultivate large bio-masses of the bacterial strain and to produce large amounts of acrylamide in an industrial scale e.g. by utilizing industrial fermentors and reactors having a large volume.

EXAMPLES

In the following, the present invention will be described in more detail. The description below discloses some embodiments and examples of the invention in such detail that a person skilled in the art is able to utilize the invention based on the disclosure. Not all steps of the embodiments are discussed in detail, as many of the steps will be obvious for the person skilled in the art based on this specification. The following examples were carried out in a small-scale testing laboratory; however, a person skilled in the art is able to scale the examples as desired.

Example 1

Isolation of a bacterial strain *Rhodococcus aetherivorans* VKM Ac-2610D being a producer of a nitrile hydratase enzyme The strain is isolated from a wastewater of acrylamide and polyacrylamide manufacture.

Composition of wastewater:

| | |
|---|---|
| Acrylamide | 6.0 g/l; |
| Acrylonitrile | 3.3 g/l; |
| $Cu^{2+}$ | 1.25 mg/l |
| $Zn^{2+}$ | 1.93 mg/l |
| $Fe^{3+}$ | 0.43 mg/l |
| Sorbital C-20 | traces. |

For isolation of the strain a selective medium was used representing an agarized wastewater having the above composition supplemented with 0.9 g/l of $Na_2HPO_4.12H_2O$, 0.5 g/l of $KH_2PO_4$, 1.0 g/l of $MgSO_4.7H_2O$, 0.5 g/l of an yeast extract. Plates with the selective medium were seeded with a lawn of 0.1 ml of a wastewater and cultivated for 72-96 hours. The grown colonies were reseeded twice on a meat and peptone agar to test purity and then they were analyzed for the ability to transform acrylonitrile to acrylamide. For this purpose the tested strains were grown in bacteriological tubes having a volume of 40 ml, ⅛-full with a medium having the following composition (g/l):

| | |
|---|---|
| $Na_2HPO_4•12H_2O$ | 0.9 |
| $KH_2PO_4$ | 0.5 |
| Glucose | 20.0 |
| Carbamide | 12.0 |
| $CoCl_2•6H_2O$ | 0.02 |
| $MgSO_4•7H_2O$ | 1.0 |
| Yeast extract | 1.0 | pH 7.0-7.4

Cultivation was carried out for 2 days with stirring, at a temperature 28-30° C. The obtained cell suspension was centrifuged for 1 minute at 15000 rpm. Cells were washed with 0.01 M phosphate buffer, pH 7.6, resuspended in 1 ml of the same buffer and then nitrile hydratase activity was measured as described in the test. This results in the strain having a nitrile hydratase activity of 95 U/mg.

Example 2

A Method of Cultivation of the Bacterial Strain *Rhodococcus aetherivorans* VKM Ac-2610D in Erlenmeyer Flasks in Laboratory Conditions Cells of the strain were grown on a meat and peptone agar slope for 36 hours at 28° C. The obtained biomass was washed out with a sterile physiological solution, pH 7.0-7.4, and seeded for a precultivation into a liquid nutrient medium of the following composition, (g/l):

| | |
|---|---|
| $Na_2HPO_4•12H_2O$ | 6.06 |
| $KH_2PO_4$ | 1.3 |
| Glucose | 12.0 |
| Carbamide | 4.0 |
| $MgSO_4•7H_2O$ | 1.0 |
| $ZnSO_4•7H_2O$ | 0.1 |
| $CaCl_2•2H_2O$ | 0.2 |
| $CoCl_2•6H_2O$ | 0.02 |
| $FeSO_4•7H_2O$ | 0.025 |
| Ascorbic acid | 0.05 |
| Distilled water | to 1 liter. | pH 7.0-7.4

The precultivation was carried out in Erlenmeyer flasks at 28-30° C., with a circular stirring of 120-160 rpm for 24-48 hours. This results in a cell suspension having an optical density of 4.6 units at λ 540 nm, 1=5 mm. The obtained suspension in the amount of 2 ml was aseptically seeded into a medium for cultivation having the following composition, g/l:

| | |
|---|---|
| $Na_2HPO_4•12H_2O$ | 6.20 |
| $KH_2PO_4$ | 1.65 |
| Glucose | 40.0 |
| Carbamide | 24.0 |
| $MgSO_4•7H_2O$ | 1.0 |
| $ZnSO_4•7H_2O$ | 0.3 |
| $CaHPO_4•2H_2O$ | 0.24 |
| $CoCl_2•6H_2O$ | 0.06 |
| $FeSO_4•7H_2O$ | 0.05 |
| Ascorbic acid | 0.10 |
| Distilled water | to 1 liter. | pH 7.0-7.4

The cultivation was carried out in Erlenmeyer flasks having a volume of 300 ml, ⅙-full with the medium, for 4 days with a circular stirring (160 rpm), at a temperature of 28-30° C. After completion of the cultivation a concentration of cells and a nitrile hydratase activity in samples was determined. The yield of cells after 96 hours of cultivation was 16.0 g/l, a specific nitrile hydratase activity was 332 U/mg at 20° C. and 521 U/mg at 25° C., a total nitrile hydratase activity was 5312 U/ml at 20° C. and 8336 U/ml at 25° C.

Determination of activity at 25° C. was carried out for comparison with a strain *Rhodococcus ruber* GT.

To confirm the scalability of the method of cultivation and a possibility of the industrial use of the bacterial strain *Rhodococcus aetherivorans* VKM Ac-2610D, a cultivation of this strain in a fermenter having a volume of 3 liters was carried out.

Example 3

Cultivation of a Bacterial Strain *Rhodococcus aetherivorans* VKM Ac-2610D in a Fermenter An inoculum representing a suspension of cells in a culture medium was prepared during 28 hours. For this purpose cells were grown with a circular stirring (160 rpm), at a temperature of 28-30° C. in Erlenmeyer flasks having a volume of 300 ml ⅙-full with the medium having the following composition, (g/l):

| | | |
|---|---|---|
| $Na_2HPO_4 \cdot 12H_2O$ | | 6.06 |
| $KH_2PO_4$ | | 1.3 |
| Glucose | | 12.0 |
| Carbamide | | 4.0 |
| $MgSO_4 \cdot 7H_2O$ | | 1.0 |
| $ZnSO_4 \cdot 7H_2O$ | | 0.1 |
| $CaCl_2 \cdot 2H_2O$ | | 0.2 |
| $CoCl_2 \cdot 6H_2O$ | | 0.02 |
| $FeSO_4 \cdot 7H_2O$ | | 0.025 |
| EDTA | | 0.05 |
| Distilled water | | to 1 liter. | pH 7.0-7.4

This resulted in a cell suspension having an optical density of 6 units at λ 540 nm, 1=5 mm. 100 ml of the obtained cell suspension were used for inoculation of a laboratory fermenter having a volume of 3 liters (filled with 1.5 l of the medium).

A composition of the medium for the fermenter, (g/l):

| | | |
|---|---|---|
| $Na_2HPO_4 \cdot 12H_2O$ | | 6.20 |
| $KH_2PO_4$ | | 1.65 |
| Glucose | | 40.0 |
| Carbamide | | 22.0 |
| $MgSO_4 \cdot 7H_2O$ | | 1.0 |
| $ZnSO_4 \cdot 7H_2O$ | | 0.25 |
| $CaHPO_4 \cdot 2H_2O$ | | 0.24 |
| $CoCl_2 \cdot 6H_2O$ | | 0.05 |
| $FeSO_4 \cdot 7H_2O$ | | 0.05 |
| EDTA | | 0.10 |
| Distilled water | | to 1 liter. | pH 7.0-7.4

The cultivation was carried out at a temperature of 28° C., an aeration of 0.5-1.0 volumes of air/volume of medium per a minute, with a continuous stirring of 560 rpm. Periodically, once at six hours, samples of the culture broth from a fermenter were taken to determine pH, a yield and nitrile hydratase activity of cells. The obtained data are presented in the table.

| | Fermentation period, hours | | | | | | |
|---|---|---|---|---|---|---|---|
| | 0 | 6 | 12 | 18 | 24 | 30 | 36 |
| pH | 7.11 | 6.95 | 6.91 | 6.88 | 6.87 | 6.88 | 6.87 |
| Yield of cells, g/l (on dry weight basis) | 0.1 | 0.4 | 1.3 | 2.4 | 3.7 | 5.5 | 7.1 |
| Specific nitrile hydratase activity, U/mg | — | 40 | 34 | 55 | 126 | 185 | 219 |

| | Fermentation period, hours | | | | | |
|---|---|---|---|---|---|---|
| | 42 | 48 | 54 | 60 | 66 | 70 |
| pH | 6.86 | 6.85 | 6.92 | 6.97 | 7.06 | 7.51 |
| Yield of cells, g/l (on dry weight basis) | 8.2 | 9.9 | 12.6 | 13.9 | 16.4 | 18.1 |
| Specific nitrile hydratase activity, U/mg | 236 | 249 | 256 | 267 | 274 | 280 |

After 70 hours of cultivation the yield of cells was 18.1 g/l, the specific nitrile hydratase activity of cells was 280 U/mg (at 20° C.) or 440 U/mg at 25° C., the total nitrile hydratase activity was 5058 U/ml (at 20° C.) or 7964 U/ml at 25° C.

Example 4

Preparation of a Concentrated Acrylamide Solution in a Laboratory Reactor Using the Cells Produced by Cultivation in Flasks 66.2 g of a cell suspension of the bacterial strain *Rhodococcus aetherivorans* VKM Ac-2610D in tap water having a nitrile hydratase activity of 270 U/mg were placed into a 150 ml thermostatic reactor supplied with a magnetic mixer and thermometer; thus, the reactor contained 30 mg (on dry weight) of the biocatalytic cells. The cells were produced as described in Example 2. pH of the reaction solution was 7.6. 24.2 g of acrylonitrile were loaded in the reactor at continuous stirring and a temperature of 17-22° C. over the whole period of synthesis so that an acrylonitrile concentration in the solution was no more than 0.3%. Acrylamide and acrylonitrile in the solution was analyzed by a gas chromatography method with a periodicity of once an hour. After 7.0 hours of synthesis the reaction was stopped because a rate of acrylonitrile hydrolysis decreased. Cells were separated from the reaction solution by centrifugation. The concentration of acrylamide in the solution was 49%, residual acrylonitrile was absent.

To confirm the possibility of using the strain *Rhodococcus aetherivorans* VKM Ac-2610D in a process of the industrial acrylamide preparation and the scalability of the claimed technology, a synthesis of acrylamide were carried out in an apparatus having a volume of 3 liters, which is an analogue of the industrial reactor.

Example 5

Synthesis of a Concentrated Acrylamide Solution in a 3 l Reactor Using the Cells Obtained by The Cultivation in Flasks 1.4 l of a cell suspension of the strain *Rhodococcus aetherivorans* VKM Ac-2610D in the desalted water having the activity of a nitrile hydratase enzyme of 254 U/mg were loaded into a 3 liter reactor supplied with a mechanical mixer and jacket for a heat removal, and thermostatically controlled in a range of temperatures 20-22° C.; thus, the reactor comprised 1 g (on dry weight) of the biocatalytic cells. The cells were obtained as described in example 2. pH of the reaction solution was 7.4. Acrylonitrile was introduced into the reaction solution as it transformation occurs so that an acrylonitrile concentration, both initial and current, was no more than 0.5%. After 5 hours of the reaction, an acrylamide solution having a concentration of 47% was obtained. Then the reaction was stopped because of the sharp decrease of the acrylonitrile hydrolysis rate.

Example 6

Preparation of a concentrated acrylamide solution in the reactor having a volume of 3 liters using the cells produced by cultivation in a fermenter 1.4 liters of a cell suspension of the strain *Rhodococcus aetherivorans* VKM Ac-2610D in the desalted water having the activity of nitrile hydratase enzyme of 280 U/mg were loaded into a 3 liter reactor supplied with a mechanical mixer and a jacket for a heat removal and thermostatically controlled in the range of temperatures of 14-23° C.; thus, the reactor comprised 1 g (on dry weight) of the biocatalytic cells. The cells were obtained as described in Example 3. pH of the reaction solution was 7.8. Acrylonitrile was introduced into the reaction solution as its transformation occurs so that an acrylonitrile concentration, both initial and current, was no more than 0.1%. Acrylamide and acrylonitrile in the solution were analyzed by a gas chromatography method with a periodicity of once in hour. After 7.0 hours the reaction was stopped because of a decrease of the acrylonitrile hydrolysis rate. The concentration of acrylamide in the solution (i.e. the final product) was 49%. A residual acrylonitrile in solution was absent.

Example 7

Preparation of a concentrated acrylamide solution in the reactor having a volume of 1 liters using the cells produced by cultivation in a fermenter having a volume of 24 liters A biomass of the bacterial strain was grown as described in the previous examples, except a fer-menter having a volume of 24 liters was used. The biomass was used to prepare acrylamide as described in the previous examples using a reactor having a volume of 1 liter. The concentration of acrylamide in the final product obtained was 49.5%. a concentration of 47-49%

It is obvious to a person skilled in the art that with the advancement of technology, the basic idea of the invention may be implemented in various ways. The invention and its embodiments are thus not limited to the examples described above, instead they may vary within the scope of the claims.

The invention claimed is:

1. A method for producing acrylamide, the method comprising hydration of acrylonitrile using a biomass of a bacterial strain belonging to the genus *Rhodococcus* and having a nitrile hydratase activity, wherein hydration is carried out at a working concentration of acrylonitrile which is no more than 0.5%, and the bacterial strain is *Rhodococcus aetherivorans* VKM Ac-2610D.

2. The method of claim 1, wherein acrylonitrile is mixed in an aqueous suspension of the biomass of the bacterial strain to form a reaction solution; and hydration is carried out so that the working concentration of acrylonitrile in the reaction solution is maintained at no more than 0.5%.

3. The method of claim 1, wherein hydration is followed by isolation of acrylamide.

4. The method of claim 1, wherein the biomass of the bacterial strain is at about 100-1000 g, or 200-1000 g, or 200-800 g, or 300-600 g, or about 400-500 g, or less than 1000 g, or less than 500 g, or less than 400 g on a dry weight of strain per 1 ton of a final product.

5. The method of claim 4, wherein the final product contains acrylamide at a concentration of at least 40%; or at least 41%; or at least 42%; or at least 43%; or at least 44%; or 40-55%; or 41-55%; 42-55%; or 43-55%; or 44-55%; or at least 45%; or at least 46%; or at least 47%; or 45-55%; or 45-54%; or 45-53%; or 45-52%; or 45-51%; or 45-50%; or 45-49%; or 46-55%; or 46-54%; or 46-53%; or 46-52%; or 46-51%; or 46-50%; or 46-49%; or 47-55%; or 47-54%; or 47-53%; or 47-52%; or 47-51%; or 47-50%; or 47-49%.

6. The method of claim 1, wherein hydration of acrylonitrile is carried out at a temperature of 10-23° C.

7. The method of claim 1, wherein hydration of acrylonitrile is carried out at a pH of 6.8-8.4.

8. The method of claim 1, wherein the biomass of the bacterial strain is at about 100-1000 g on a dry weight of strain per 1 ton of a final product.

9. The method of claim 1, wherein the biomass of the bacterial strain is at about 200-1000 g on a dry weight of strain per 1 ton of a final product.

10. The method of claim 1, wherein the biomass of the bacterial strain is at about 200-800 g on a dry weight of strain per 1 ton of a final product.

11. The method of claim 1, wherein the biomass of the bacterial strain is at about 300-600 g on a dry weight of strain per 1 ton of a final product.

12. The method of claim 1, wherein the biomass of the bacterial strain is at about 400-500 g on a dry weight of strain per 1 ton of a final product.

13. The method of claim 1, wherein the biomass of the bacterial strain is less than 1000 g on a dry weight of strain per 1 ton of a final product.

14. The method of claim 1, wherein the biomass of the bacterial strain is less than 500 g on a dry weight of strain per 1 ton of a final product.

15. The method of claim 1, wherein the biomass of the bacterial strain is less than 400 g on a dry weight of strain per 1 ton of a final product.

16. The method of claim 4, wherein the final product contains acrylamide at a concentration of 47-55%.

17. The method of claim 4, wherein the final product contains acrylamide at a concentration of 47-54%.

18. The method of claim 4, wherein the final product contains acrylamide at a concentration of 47-52%.

19. The method of claim 4, wherein the final product contains acrylamide at a concentration of 47-52%.

20. The method of claim 4, wherein the final product contains acrylamide at a concentration of 47-49%.

* * * * *

UNITED STATES PATENT AND TRADEMARK OFFICE
CERTIFICATE OF CORRECTION

PATENT NO.        : 9,518,279 B2                                              Page 1 of 1
APPLICATION NO.   : 14/140150
DATED             : December 13, 2016
INVENTOR(S)       : Kozulin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 162 days.

Signed and Sealed this
Twenty-fifth Day of September, 2018

Andrei Iancu
*Director of the United States Patent and Trademark Office*